United States Patent [19]

Dosako et al.

[11] Patent Number: 5,061,622

[45] Date of Patent: Oct. 29, 1991

[54] PROCESS FOR THE PRODUCTION OF KAPPA-CASEIN GLYCOMACROPEPTIDE

[75] Inventors: Shunichi Dosako, Urawa; Tsuguaki Nishiya; Eiki Deya, both of Sayama, all of Japan

[73] Assignee: Snow Brand Milk Products Co., Ltd., Sapporo, Japan

[21] Appl. No.: 191,140

[22] Filed: May 6, 1988

[30] Foreign Application Priority Data

May 15, 1987 [JP] Japan .................................. 62-118611

[51] Int. Cl.$^5$ .......................... C12P 21/06; A23J 3/00
[52] U.S. Cl. .................................... 435/68.1; 426/39; 426/40; 426/42
[58] Field of Search .................. 435/68.1; 426/39, 40, 426/42

[56] References Cited

U.S. PATENT DOCUMENTS

| | | | |
|---|---|---|---|
| 2,473,255 | 6/1949 | Parfentjev | 435/68.1 X |
| 3,803,327 | 4/1974 | Fujimaki et al. | 435/68.1 X |
| 3,970,520 | 7/1976 | Feldman et al. | 435/68.1 X |
| 4,197,322 | 4/1980 | Middleton | 426/40 X |
| 4,213,896 | 7/1980 | Davis | 530/360 |
| 4,358,465 | 11/1982 | Brule et al. | 435/68.1 |
| 4,409,248 | 10/1983 | Lehnhardt et al. | 435/68.1 X |
| 4,452,888 | 6/1984 | Yamazaki et al. | 435/68.1 |
| 4,691,011 | 9/1987 | Inagami et al. | 530/833 X |
| 4,822,623 | 4/1989 | Middleton | 426/40 X |

FOREIGN PATENT DOCUMENTS

| | | | |
|---|---|---|---|
| 291264 | 11/1988 | European Pat. Off. | 435/68.1 |
| 198398 | 9/1987 | Japan | 435/68.1 |

*Primary Examiner*—Carolyn Elmore
*Attorney, Agent, or Firm*—Oblon, Spivak, McClelland, Maier & Neustadt

[57] ABSTRACT

Disclosed herein is a process for the efficient production of κ-casein GMP on an industrial scale. The production of high-purity κ-casein GMP is realized by using an effluent of rennet-casein curd free of whey proteins, lactose and the like as a starting effluent, adjusting the pH of the effluent to an acidic range to remove calcium phosphate and then subjecting the resulting effluent to a desalting treatment. κ-Casein GMP is used as a standard substance for the assay of sialic acid. It has also attracted attention for its physiological activities and other properties.

10 Claims, No Drawings

PROCESS FOR THE PRODUCTION OF KAPPA-CASEIN GLYCOMACROPEPTIDE

BACKGROUND OF THE INVENTION

1. Field of the Invention

This invention relates to a process for the production of κ-casein glycomacropeptide useful as a sialic-acid-conjugating sialic acid standard composition, which is used in assay kits for sialic acid, or as an infection protectant.

2. Description of the Prior Art

κ-Casein glycomacropeptide (hereinafter abbreviated as "κ-casein GMP") is a sialic-acid-conjugating peptide which is formed when rennin or pepsin is caused to act on κ-casein in cow's milk. Cheese whey has been known for many years to contain κ-casein GMP.

As a production method of κ-casein GMP, it has been practised as a laboratory study to prepare κ-casein GMP, for example, by causing pepsin to act on a solution of κ-casein, which has been isolated from cow's milk, in deionized water, adding trichloroacetic acid to precipitate the para-κ-casein fraction, dialyzing the resultant supernatant liquid against deionized water to desalt same, and then lyophilizing the resultant dialysate [Stan et al., "Bulletin of Experimental Biology and Medicine", 96, 889 (1983)] or by dissolving the above-mentioned κ-casein in deionized water, adjusting the pH of the resultant solution to 6.7, causing rennet to act on the κ-casein, adjusting the pH of the solution to 4.6 to precipitate and remove para-κ-casein, subjecting the resultant supernatant liquid to dialysis to desalt same, and then lyophilizing the thus-prepared solution ["Milk Protein", page 200, Academic Press Inc.].

These methods are, however, for laboratory study and obviously cannot be said suitable for mass production.

On the other hand, no investigation has been made regarding the process for its mass production because no industrial utility has been known to date with respect to κ-casein GMP.

It has however been reported recently that κ-casein GMP is effective in lowering the appetite of dogs [Stan et al., "Bulletin of Experimental Biology and Medicine", 96, 889 (1983)]. It has hence been found that κ-casein GMP can be used as a food additive for the prevention of overweight.

It has also been found that κ-casein GMP is extremely effective as a standard composition for a kit for the assay of sialic acid. Besides, its various physiological activities are expected to find utility. There is hence an outstanding demand for its production on an industrial scale.

BRIEF SUMMARY OF THE INVENTION

With the foregoing in view, the present invention has a principal object: the provision of a process for the efficient production of κ-casein GMP on an industrial scale.

The principal feature of this invention lies in the production of κ-casein GMP from a raw material which has been obtained by using as a starting material an effluent available upon preparation of rennet-casein curd, adjusting the pH of the effluent to an acidic range, removing the resultant precipitate, and then subjecting the thus-prepared supernatant liquid to a desalting treatment.

DETAILED DESCRIPTION AND THE PREFERRED EMBODIMENTS:

Since the selection of a raw material is extremely important for the economical mass production of κ-casein GMP, a variety of raw materials was studied in the present invention. As a result, it has become feasible to conduct its mass production advantageously by using an effluent, which has been obtained upon preparation of rennet-casein curd, as a raw material and then recovering κ-casein GMP contained in the effluent. As a method for forming rennet-casein curd and obtaining an effluent, it may be mentioned to subject a casein such as acid casein, sodium caseinate, calcium caseinate or the like to an enzymatic milk-coagulating treatment with rennin and/or pepsin and then to remove the resulting coagulum (rennet-casein) by decantation, centrifugation, filtration or the like. Whichever starting material is used, it is a casein. It is hence free of whey proteins, lactose and the like, so that the subsequent steps can be simplified. As preferred starting materials, acid casein, sodium caseinate and calcium caseinate may be mentioned. One or more of these caseins are subjected to a milk-coagulating treatment by using rennin and/or pepsin and if necessary, by adding divalent metal ions to make a suitable concentration, whereby rennet-casein curd is formed. An effluent also formed at the same time is used as a raw material. An effluent (whey) known in general, for example, cheese whey is known to contain GMP. Hence using this whey as a raw material may be contemplated. The whey however contains various whey proteins in addition to GMP, thereby making it difficult as a matter of fact to recover high-purity GMP. Using κ-casein as a raw material instead of whey may also be contemplated. Although a process has been proposed for the industrial isolation of κ-casein from milk (Japanese Patent Laid-Open No. 91,848/1984), this process requires gel filtration and cannot hence avoid a high production cost. Therefore, the process making use of κ-casein as a raw material has low practical utility.

The use of an effluent useful in the practice of this invention is free of problems such as those mentioned above. Although the effluent has an advantage that it contains neither whey proteins nor lactose, it contains a great deal of calcium phosphate like cheese whey. Since calcium phosphate is substantially insoluble, the use of the effluent involves a problem that the subsequent steps for the recovery of κ-casein GMP are very difficult to perform.

In the present invention, as a method for removing calcium phosphate from the effluent, the pH of the effluent is adjusted to an acidic range, preferably, to 4–5 so that calcium phosphate can be precipitated and removed effectively.

As a cause for this precipitation of calcium phosphate, it may be mentioned that when small amounts of coexistent casein and decomposition products of casein other than κ-casein GMP remaining in the effluent undergo isoelectric precipitation, they probably precipitate with calcium phosphate contained therein.

Namely, the solubility itself of calcium phosphate is substantially independent on the above pH adjustment. However, the above-mentioned coexistent casein fragments seem to precipitate along with calcium phosphate contained therein upon precipitation of the casein fragments at a pH in the acidic range.

It is preferable to heat the effluent to about 40°–50° C. and maintain it in order to promote the formation of the above-mentioned precipitate in the effluent. Centrifugal separation or filter filtration may be used preferably for the removal of the resultant precipitate. A general clarifier may be used for the centrifugal separation, while the filter filtration may be effected by using a filter press and microfilter either singly or in combination.

A supernatant liquid which has been obtained by removing the above precipitate from the effluent is desalted or concentrated and desalted, preferably after readjusting its pH to neutral. Namely, the supernatant liquid obtained as described above has a high ash content and the purity of the resulting κ-casein GMP is lowered accordingly. When the liquid is added to foods, it is difficult to adjust their mineral balance due to the excess mineral contents. When κ-casein GMP is used as powder on the other hand, the efficiency of the drying step for the liquid is low because its concentration in the liquid is low.

The above concentration may be effected by vacuum evaporation, heat concentration, concentration making use of a reverse osmosis membrane (RO membrane) or the like, while the desalting may be conducted by using an ion-exchange resin, electrodialysis (ED) or an RO membrane. The use of an RO membrane is effective because the concentration and desalting can be performed at the same time.

The supernatant which has been subjected to the above concentration and desalting may be subjected to sterilization, followed by spray drying, freeze-drying or the like.

κ-Casein GMP obtained as described above has a purity of at least 80%, a sialic acid content of at least 5% and an ash content up to 10%, so that high-quality κ-casein GMP can be obtained.

As has been mentioned above, according to this invention, an economical effluent formed upon preparation of rennet-casein is used as a raw material and high-purity κ-casein GMP can be obtained. It is hence possible to produce the κ-casein GMP on an industrial scale. Thus, this is advantageous for the utilization of κ-casein.

The present invention will hereinafter be described specifically with reference to the figures.

EXAMPLE 1

After dissolving 30 kg of sodium caseinate in 330 l of warm water of 50° C., the resultant solution was cooled to 37° C. and maintained constant at that temperature. The pH of the solution was thereafter adjusted to 6.4 with concentrated hydrochloric acid and a 30% aqueous solution of caustic soda. Rennet (22 g; product of Hansen Company) was added, followed by hydrolysis for 15 minutes. After the hydrolysis, 4.4 kg of calcium chloride and 560 g of lactic acid of 88% purity were added, followed by thorough mixing. Resulting curd was removed to obtain a supernatant liquid. The pH of the liquid was 4.8. The supernatant liquid was heated at 90° C. for 10 minutes to inactivate the enzyme and then cooled to 40° C. Using a reverse osmosis membrane ("MRG-20", trade name; product of Mitsubishi Rayon Co., Ltd.), the liquid was desalted and concentrated with 5 times its volumes of deionized water to obtain 50 l of a concentrated solution. It was concentrated further to 10 l in an evaporator and then freeze-dried, thereby obtaining 1.3 kg of κ-casein GMP composition as powder.

As a result of an analysis of the powder by electrophoresis, the purity of κ-casein GMP was found to be 82 wt. %, the ash content 9.8 wt. %, and the content of sialic acid in the powder 5.2 wt. %.

EXAMPLE 2

Five kilograms of lactic caseinate was added to 200 l of warm water of 70° C. In a homogenizer, the lactic caseinate was dissolved while maintaining the solution at pH 7 with a 30% aqueous solution of caustic soda. The resultant solution was then maintained at 37° C. Thereafter, the pH of the solution was adjusted to 6.5 with concentrated hydrochloric acid and a 30% aqueous solution of caustic acid. Rennet (4.5 g; product of Hansen Company) was added, followed by hydrolysis for 30 minutes. After the hydrolysis, 650 g of calcium chloride and 85 g of lactic acid of 88% purity were added, followed by thorough mixing. Resulting curd was removed to obtain a supernatant liquid. Because the pH of the liquid was 5.2, hydrochloric acid was added to adjust its pH to 4.6. The supernatant liquid was heated at 75° C. for 30 minutes to inactivate the enzyme and then cooled to 40° C. Using a reverse osmosis membrane ("MRG-20", trade name; product of Mitsubishi Rayon Co., Ltd.), the liquid was desalted and concentrated with 5 times its volumes of deionized water to obtain 50 l of a concentrated solution. It was concentrated further to 10 l in an evaporator and then freeze-dried, thereby obtaining 162 g of κ-casein GMP composition.

EXAMPLES 3-5

Following the procedure of Example 1, κ-casein GMP solutions were separately obtained under the conditions given in Table 1. The compositions of their dry products were analyzed. The purities of the respective κ-casein GMP samples are also given in Table 1.

COMPARATIVE EXAMPLES 1-3

The procedure of Example 1 was repeated under the conditions also given in Table 1. Although white powders were obtained respectively, their analysis results were not satisfactory at all because of lower purity of κ-casein GMP, higher ash content, and lower content of sialic acid.

TABLE 1

| | Starting material | pH of effluent | Coexistent divalent ions | Composition (as dry product) | | |
|---|---|---|---|---|---|---|
| | | | | Purity of κ-casein GMP wt. % | Ash content wt. % | Sialic acid wt. % |
| Example | | | | | | |
| 3 | Calcium caseinate | 4.5 | None | 78 | 10.5 | 4.8 |
| 4 | Lactic caseinate | 4 | Ca$^{++}$ | 83 | 11 | 5.2 |
| 5 | Sodium caseinate | 4.5 | Mg$^{++}$ | 80.5 | 11 | 5.0 |
| Comp. Ex. | | | | | | |
| 1 | Sodium caseinate | 5.5 | Ca$^{++}$ | 58 | 28 | 3.5 |
| 2 | Sodium caseinate | 5.5 | None | 3.1 | 8.3 | 0.2 |

TABLE 1-continued

| | Starting material | pH of effluent | Coexistent divalent ions | Composition (as dry product) | | |
|---|---|---|---|---|---|---|
| | | | | Purity of κ-casein GMP wt. % | Ash content wt. % | Sialic acid wt. % |
| 3 | Sodium caseinate | 3.5 | $Ca^{++}$ | 64 | 18 | 3.9 |

We claim:

1. A process for the production of κ-casein glycomacropeptide, which comprises the steps of:
   (a) adding divalent metal ions to a casein and subjecting said casein to an enzymatic milk-coagulating rennin treatment to obtain a rennet-casein curd and non-coagulant components as an effluent,
   (b) separating the effluent from the rennet-casein curd,
   (c) acidifying the effluent to a pH sufficient to form a precipitate,
   (d) removing the precipitate from the effluent, and then subjecting the effluent to a concentration and desalting treatment.

2. The process as claimed in claim 1, wherein the casein is acid casein, sodium caseinate, or calcium caseinate.

3. The process as claimed in claim 1, wherein the effluent is acidified to a pH of 4–5 during the acidfying step.

4. The process of claim 1, wherein said effluent is heated to about 40°–50° C. during said acidifying step.

5. The process of claim 1, wherein said effluent is subjected to a desalting treatment immediately after removing said precipitate from said effluent.

6. The process of claim 5, wherein said desalting treatment comprises an ion-exchange resin, electrodialysis or a reverse osmosis membrane.

7. The process of claim 1, wherein after removing the precipitate from said effluent, the pH of said effluent is adjusted to neutral and then said neutral effluent is subjected to a desalting treatment.

8. The process of claim 1, wherein the pH during said rennin treatment is a pH at which rennin is enzymatically active.

9. The process of claim 8, wherein said pH is 6.4–6.5.

10. The process of claim 1, wherein said precipitate comprises calcium phosphate and casein decomposition products.

* * * * *